US012797107B2

(12) United States Patent
Wei

(10) Patent No.: US 12,797,107 B2
(45) Date of Patent: Nov. 17, 2026

(54) BALLOON CATHETER FOR LINEAR SEGMENTATION OF GLAND TISSUE

(71) Applicant: QINGDAO BIOTECH MEDICAL CO., LTD, Qingdao (CN)

(72) Inventor: Yan Wei, Qingdao (CN)

(73) Assignee: QINGDAO BIOTECH MEDICAL CO., LTD, Qindao (CN)

( * ) Notice: Subject to any disclaimer, the term of this patent is extended or adjusted under 35 U.S.C. 154(b) by 232 days.

(21) Appl. No.: 18/566,275

(22) PCT Filed: May 27, 2022

(86) PCT No.: PCT/CN2022/095541

§ 371 (c)(1),
(2) Date: Jun. 12, 2024

(87) PCT Pub. No.: WO2022/253129

PCT Pub. Date: Dec. 8, 2022

(65) Prior Publication Data

US 2025/0195101 A1 Jun. 19, 2025

(30) Foreign Application Priority Data

Jun. 1, 2021 (CN) ......................... 202110607643.2

(51) Int. Cl.
*A61B 17/3207* (2006.01)
*A61M 25/10* (2013.01)
*A61B 17/22* (2006.01)

(52) U.S. Cl.
CPC ................. *A61B 17/320725* (2013.01); *A61B 2017/22061* (2013.01); *A61M 2025/1084* (2013.01); *A61M 2025/109* (2013.01)

(58) Field of Classification Search
CPC ...... A61B 17/320725; A61B 17/22061; A61B 17/22051; A61M 2025/1086; A61M 2025/109; A61M 25/10; A61M 25/104
See application file for complete search history.

(56) References Cited

U.S. PATENT DOCUMENTS

| | | | |
|---|---|---|---|
| 5,797,935 | A | 8/1998 | Barath |
| 2003/0229370 | A1 | 12/2003 | Miller |

(Continued)

FOREIGN PATENT DOCUMENTS

| | | | |
|---|---|---|---|
| CN | 103949002 A | 7/2014 | |
| CN | 104159541 A | 11/2014 | |

(Continued)

OTHER PUBLICATIONS

First Office Action issued in counterpart Chinese Patent Application No. 202110607643.2, dated Dec. 16, 2024.

(Continued)

*Primary Examiner* — Kathleen S Holwerda
(74) *Attorney, Agent, or Firm* — Westbridge IP LLC

(57) ABSTRACT

A balloon catheter for linear segmentation of gland tissue includes a balloon body, an elastic connector and a linear segmentation part, a middle portion of the elastic connector is fixed on a surface of the balloon body, the linear segmentation part is provided in the middle portion of the elastic connector, two ends of the elastic connector are fixedly connected with two ends of the balloon body respectively, and a position between the middle portion of the elastic connector and an end portion of the elastic connector is separated from the balloon body. Through the present disclosure, the technical problems of a poor effect and poor applicability of cutting a balloon on expansion of a hyperplastic gland are solved.

7 Claims, 4 Drawing Sheets

(56) References Cited

U.S. PATENT DOCUMENTS

| | | | | |
|---|---|---|---|---|
| 2004/0133223 | A1* | 7/2004 | Weber ............ | A61B 17/320725 606/159 |
| 2005/0228343 | A1 | 10/2005 | Kelley | |
| 2005/0245864 | A1 | 11/2005 | O'brien et al. | |
| 2006/0111736 | A1* | 5/2006 | Kelley ........... | A61B 17/320725 606/159 |
| 2008/0300610 | A1 | 12/2008 | Chambers | |
| 2011/0152905 | A1 | 6/2011 | Eaton | |
| 2017/0319231 | A1 | 11/2017 | Nishigishi et al. | |
| 2019/0344054 | A1 | 11/2019 | Slattery et al. | |

FOREIGN PATENT DOCUMENTS

| | | | |
|---|---|---|---|
| CN | 107405473 | A | 11/2017 |
| CN | 108577937 | A | 9/2018 |
| CN | 109893215 | A | 6/2019 |
| CN | 209122369 | U | 7/2019 |
| CN | 211300215 | U | 8/2020 |
| CN | 111699016 | A | 9/2020 |
| CN | 112472228 | A | 3/2021 |
| CN | 213129744 | U | 5/2021 |
| CN | 113425380 | A | 9/2021 |
| CN | 215821087 | U | 2/2022 |

OTHER PUBLICATIONS

Extended European Search Report issued in counterpart European Patent Application No. 22815175.9, dated May 12, 2025.

Second Office Action issued in counterpart Chinese Patent Application No. 202110607643.2, dated Apr. 30, 2025.

International Search Report issued in corresponding PCT Application No. PCT/CN2022/095541, dated Apr. 17, 2022.

Search Report issued in counterpart Chinese Patent Application No. 202110607643.2, dated Jun. 30, 2022.

Written Opinion issued in corresponding PCT Application No. PCT/CN2022/095541, dated Aug. 17, 2022.

Refusal Decision issued in counterpart Chinese Patent Application No. 202110607643.2, dated Jul. 28, 2025.

* cited by examiner

BALLOON CATHETER FOR LINEAR SEGMENTATION OF GLAND TISSUE

CROSS-REFERENCE TO RELATED APPLICATIONS

This application is the National Stage of International Application No. PCT/CN2022/095541, filed May 27, 2022, which claims priority to Chinese Patent Application No. 202110607643.2, filed Jun. 1, 2021, both of which are hereby incorporated by reference in their entireties.

TECHNICAL FIELD

The present disclosure relates to the field of medical instruments, in particular to a balloon catheter for linear segmentation of gland tissue.

BACKGROUND

With the development of the balloon dilatation technology, a cutting balloon as an important branch of the field of vascular dilation has also been developed rapidly. The cutting balloon is to cut an atherosclerotic plaque on an inner wall of a blood vessel via balloon dilatation, by using a micro-blade carried on a surface of a balloon, and for a narrow blood vessel with sclerotic plaque which cannot be dilated by a common balloon, the cutting balloon usually can obtain a better effect by performing incisions on atherosclerotic plaques on the inner walls of blood vessels through balloon angioplasty.

The principle of the cutting balloon is, during balloon dilation, to cut a blood vessel wall having a sclerotic plaque by concentrating an expansion stress on a blade on a surface of a balloon, so that a diseased blood vessel can be dilated without a need of applying an extreme dilating pressure to the balloon. A process of balloon dilation on a blood vessel is irregular, thus with the increase of a balloon dilation pressure, a damage rate of the balloon dilation on a blood vessel wall will increase, hence the cutting balloon requires a smaller dilating pressure than a conventional balloon, so as to produce a better dilating effect on a vascular disease and obtain better clinical curative effect.

Currently, the use of balloon angioplasty for expanding hyperplastic glands tissue in patients (such as cervical gland, prostate gland and esophageal gland) has become increasingly common for treatmenting proliferative narrow diseases. A glandular tissue contains a large number of fiber muscles, after dilatation of a hyperplastic narrow gland through a common balloon, the fiber muscles with a high density of the glandular tissue will produce large rebound, resulting in narrow “blockage” of a dilated space again, thus if dilation of a common balloon wants to achieve a better dilation effect, it is necessary to select a balloon having a larger size according to a gland hyperplasia volume, meanwhile an extreme dilating pressure must be applied on the gland through balloon dilation. Since a stress at the time of balloon dilation is disordered, constantly adding a pressure to dilate a gland often leads to multiple lacerations or bleeding of the gland, even damages glandular nerves to cause severe postoperative pain, bringing great suffering to patients, the actual use effect is not ideal, which also leads to still clinically more use of the mode of multiple repeated dilations so as to gradually obtain a desired dilation effect.

There are two main modes to prepare a cutting balloon in prior arts, one is to fixedly mount a blade on a balloon surface, however for this mode, the blade is usually installed on a base first, and then the base is glued to the balloon surface, because the blade base and a high-pressure dilation balloon body are made of hard materials, there is a risk of unstable fixation of the blade base; the other is to separate a sharp cutting protrusion of the blade from a balloon, the cutting protrusion is fixedly connected by extending into slots of proximal and distal connecting pipes of the balloon, although this mode has no risk of unstable fixation of the cutting protrusion and the balloon surface, but since the cutting protrusion and the balloon are not fixedly connected, it is easy to cause a risk of displacement of the cutting protrusion during dilation, meanwhile for this mode, in order to cooperate with a deformation produced by dilation and swelling of the balloon, a length of a cutting protrusion component must be longer than an overall length of the balloon, which results in accumulation of redundant cutting protrusion components at both ends of the balloon at the time of a balloon contraction state, causes a contraction size of the balloon to be larger, and is not conducive for the balloon in contraction state to pass through a narrow diseased region. Moreover, the above two kinds of cutting balloons have the problems of complex production process and high cost, which is not conducive to scale production.

For the problems of poor dilation of a hyperplastic gland by the cutting balloon with poor applicability in related techniques, currently, no effective solution has been given.

SUMMARY

The purpose of the present disclosure is to provide a balloon catheter for linear segmentation of gland tissue, capable of performing effective linear segmentation of a hyperplastic gland without a need for an extreme dilating pressure, greatly reducing damage to a gland in a circumferential direction during dilation and compressive rebound after a hyperplastic gland tissue is dilated, realizing effective dilation of the hyperplastic gland, obtaining an ideal dilated cavity space, and greatly improving a surgical efficiency and a postoperative effect.

The purpose of the present disclosure may be realized by using the following technical solution.

The present disclosure provides a balloon catheter for linear segmentation of gland tissue, comprising a balloon body, an elastic connector and a linear segmentation part, in which:

- a middle portion of the elastic connector is fixed on a surface of the balloon body, the linear segmentation part is provided in the middle portion of the elastic connector, two ends of the elastic connector are fixedly connected with two ends of the balloon body respectively, and a position between the middle portion of the elastic connector and an end portion of the elastic connector is separated from the balloon body.

Advantageous effects of the present disclosure are as follows.

1. The balloon catheter for linear segmentation of gland tissue can produce a stable linear segmentation part stress on the glandular tissue when the balloon body is dilated, promote linear cracking of the glandular tissue at a stress concentration site without additionally increasing a pressure on the balloon body, thereby to produce an ideal dilation effect and obtain an ideal dilated cavity space.
2. The balloon catheter for linear segmentation of gland tissue, during use, can avoid random tearing injury of the glandular tissue in a circumferential direction due to an irregular stress caused by high-pressure dilation of the balloon body, thereby to obtain better clinical curative effect.

3. Providing an elastic connector in the balloon catheter for linear segmentation of gland tissue can greatly improve stability of a connection between a highly rigid linear segmentation part and the balloon body, effectively prevent displacement and falling of the linear segmentation part due to glandular tissue extrusion during dilation of the balloon body, meanwhile can avoid occurrence of balloon leakage due to damage by the linear segmentation part to the balloon body during dilation of the balloon body.
4. In the balloon catheter for linear segmentation of gland tissue, a gasket and a sleeve ring are connected via an elastic tendon, which ensures that there is enough swelling space when balloon body is dilated at the same of ensuring that a minimum diameter size can be obtained when the balloon body is in a contracted state; moreover, a fixed connection between the sleeve ring and the balloon body can further enhance stability and safety of fixing the gasket on a surface of a dilated straight working segment of the balloon body, meanwhile facilitating assembly and suiting for industrial manufacturing.

BRIEF DESCRIPTION OF THE DRAWINGS

The following drawings are intended only to schematically illustrate and explain the present disclosure and do not limit the scope of the present disclosure. In the drawings.

DETAILED DESCRIPTION OF THE EMBODIMENTS

In order to have a clearer understanding on the technical features, purpose and effect of the present disclosure, the specific embodiments of the present disclosure are illustrated with reference to the drawings.

Figure 1:
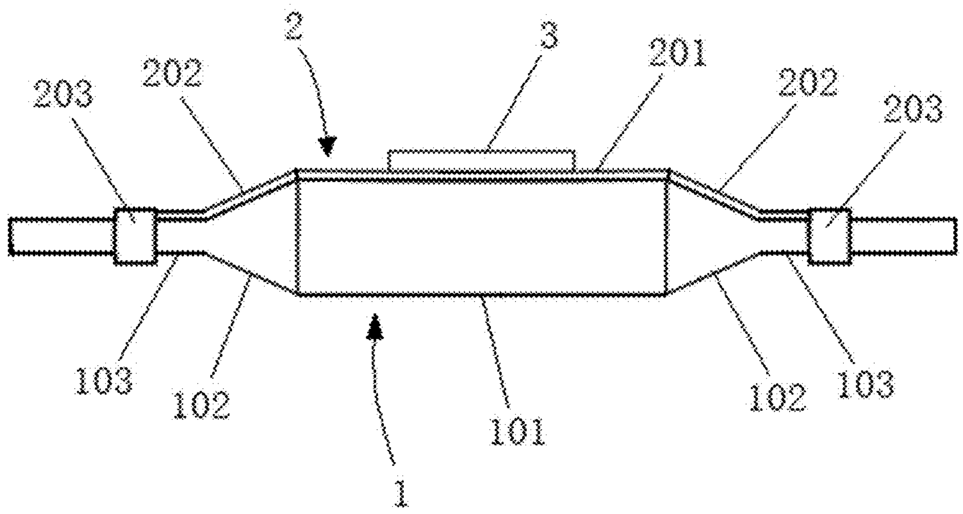
FIG. 1: a front view of a balloon catheter for linear segmentation of gland tissue in the present disclosure.
Figure 2:
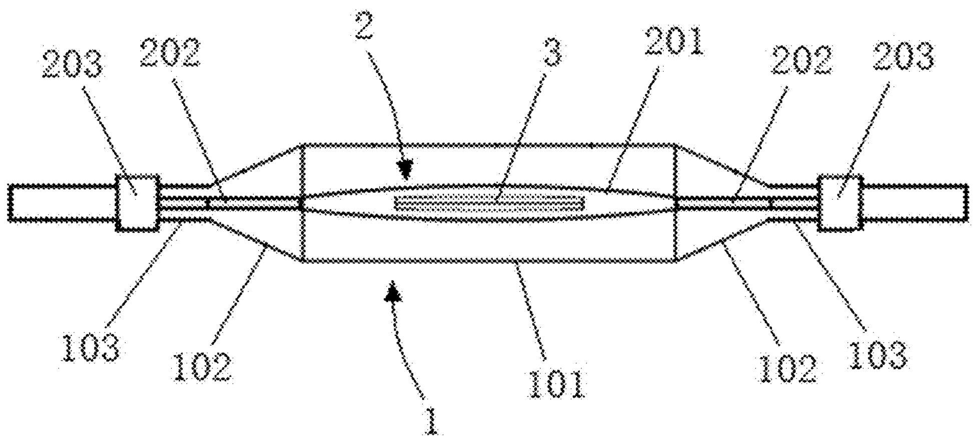
FIG. 2: a top view of a balloon catheter for linear segmentation of gland tissue in the present disclosure.

As shown in FIGS. 1 and 2, the present disclosure provides a balloon catheter for linear segmentation of gland tissue, including a balloon body 1, an elastic connector 2 and a linear segmentation part 3, in which a middle portion of the elastic connector 2 is fixed on a surface of the balloon body 1, the linear segmentation part 3 is provided in the middle portion of the elastic connector 2, two ends of the elastic connector 2 are fixedly connected with two ends of the balloon body 1 respectively, and a position between the middle portion of the elastic connector 2 and an end portion of the elastic connector 2 is separated from the balloon body 1.

In the present disclosure, during the use of the balloon catheter for linear segmentation of gland tissue, can produce a stable linear segmentation stress on the glandular tissue when the balloon body 1 is dilated, promote linear cracking of the glandular tissue at a stress concentration site without additionally increasing a pressure on the balloon body 1, thereby to produce an ideal dilation effect and obtain an ideal dilated cavity space; during the use of the balloon catheter for linear segmentation of gland tissue, can avoid random tearing injury of the glandular tissue in a circumferential direction due to an irregular stress caused by high-pressure dilation 1 of the balloon body, thereby to obtain better clinical curative effect; providing an elastic connector 2 in the present disclosure can greatly improve stability of a connection between a highly rigid linear segmentation part 3 and the balloon body 1, effectively prevent displacement and falling of the linear segmentation part 3 due to glandular tissue extrusion during dilation of the balloon body 1, meanwhile can avoid occurrence of leakage of the balloon body 1 due to damage by the linear segmentation part 3 to the balloon body 1 during dilation of the balloon body 1.

Further, as shown in FIGS. 1 and 2, a length of the elastic connector 2 in an axial direction of the balloon body 1 is less than an axial length under a contraction state of the balloon body 1.

Exemplarily, a length of the elastic connector 2 in an axial direction of the balloon body 1 is less than an axial length by 0.5 mm to 20 mm under a contraction state of the balloon body 1.

In an optional embodiment of the present disclosure, as illustrated in FIG. 1 and FIG. 2, the balloon body 1 includes a dilated straight working segment 101, two transition segments 102 and two thin-neck straight segments 103, the two transition segments 102 are respectively located on two sides of the extended straight working segment 101, one end of each of the two transition segments 102 are connected with two ends of the dilated straight working segment 101 respectively, and the other end of each of the two transition segments 102 are connected with corresponding thin-neck straight segments 103 respectively; in which a diameter of the dilated straight working segment 101 is greater than a diameter of the thin-neck straight segments 103, and a diameter of the transition segments 102 gradually decreases in a direction from the dilated straight working segment 101 to the thin-neck straight segments 103.

Figure 6:
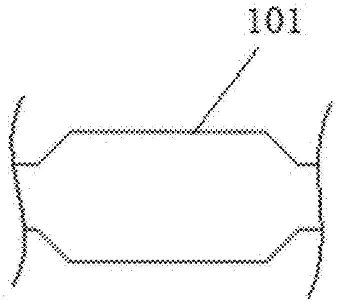
FIG. 6: a first structure diagram of a working segment of a balloon body in a balloon catheter for linear segmentation of gland tissue in the present disclosure.
Figure 7:
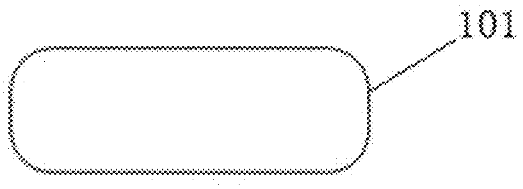
FIG. 7: a second structure diagram of a working segment of a balloon body in a balloon catheter for linear segmentation of gland tissue in the present disclosure.
Figure 8:
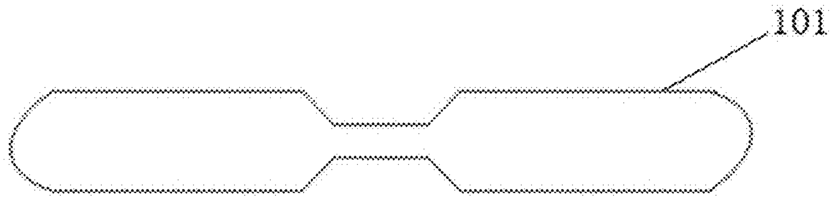
FIG. 8: a third structure diagram of a working segment of a balloon body in a balloon catheter for linear segmentation of gland tissue in the present disclosure.

Further, as shown in FIG. 6 to FIG. 8, the balloon body 1 may be but is not limited to conical or cylindrical. Of course, the balloon body 1 may also be a special-shaped columnar structure (such as: a dumbbell structure with a large diameter at both ends and a small diameter in the middle).

Further, the dilated straight working segment 101, the transition segments 102 and the thin-neck straight segments 103 may be but are not limited to an integrally-formed structure.

Further, the balloon body 1 (i.e., the dilated straight working segment 101, the transition segments 102 and the thin-neck straight segments 103) is made of a high molecular material.

Further, the balloon body 1 may be a single layer structure, the high molecular material used for the balloon body

1 having the single layer structure is any one of the group consisting of polyvinyl chloride, nylon, modified nylon and Pebax (a thermoplastic elastomer without containing a plasticizer); the balloon body 1 may also be a multilayered structure, the high molecular material used for the balloon body 1 having the multilayered structure is any one of the group consisting of polyvinyl chloride, nylon, modified nylon and Pebax.

In an optional embodiment of the present disclosure, as illustrated in FIG. 1 and FIG. 2, the elastic connector 2 includes a gasket 201, two elastic tendons 202 and two sleeve rings 203, the gasket 201 is fixed on a surface of the dilated straight working segment 101, the two sleeve rings 203 are fixedly sleeved on the corresponding thin-neck straight segments 103 respectively, one of the elastic tendons 202 is connected between an end of the gasket 201 and one of the sleeve rings 203, and the other one of the elastic tendons 202 is connected between the other end of the gasket 201 and the other one of the sleeve rings 203, the two elastic tendons 202 are located respectively in a position axially opposite to the two transition segments 102 of the balloon body 1, and the two elastic tendons 202 are separated from the corresponding transition segments 102 so that the elastic connector 2 is in an active state. When the balloon body 1 is in a contraction state, the elastic tendons 202 keep a horizontal contraction state consistent with the balloon body 1, so as to minimize a contraction size of the balloon body 1 and effectively improve the passage performance of the balloon body 1 in a narrow diseased position; when the balloon body 1 is in a dilation and swelling state, the elastic tendons 202 stretches to become longer with the dilation and swelling of the balloon body 1, so as to provide sufficient size guarantee for a deformation of the balloon body 1 during dilation and swelling.

In the present disclosure, by fixing the elastic gasket 201 on a surface of the balloon body 1, a single linear segmentation part 3, assisted by dilation of the balloon body 1, can provide a stable linear segmentation stress to a glandular tissue, so that when the balloon body 1 is dilated, the glandular tissue cracks linearly at a stress concentration site, to effectively prevent displacement of the linear segmentation part 3 because the glandular tissue is extruded during dilation of the balloon body 1, thereby to avoid a failure of linear segmentation. At the same time, the single linear segmentation part 3 can ensure that a damage to the glandular tissue is minimized, and a single linear crack generated is conducive to rapid recovery of the glandular tissue after a surgery, so as to obtain the best clinical curative effect. Of course, the number of the elastic connectors 2 and the number of the linear segmentation parts 3 may also be multiple, each elastic connector 2 is arranged in a circumferential direction of the balloon body 1, the middle portion of each elastic connector 2 is provided with the linear segmentation part 3. The number of the elastic connectors 2 and a position in a circumferential direction of the balloon body 1 can be set according to an actual situation (such as a position where a glandular tissue needs to be partitioned) so as to meet the operational requirements.

Further, the elastic connector 2 (i.e., the gasket 201, the elastic tendons 202 and the sleeve rings 203) may be made of, but not limited to, plastic with viscoelasticity. Since the gasket 201 has excellent viscoelasticity, the balloon body 1 can serve as a stress buffer when being fully dilated, which can disperse a linear stress generated by the linear segmentation part 3 on a surface of the balloon body 1 and prevent a damage or leakage of the balloon body 1 caused by linear stress concentration. Moreover, since the gasket 201 has excellent viscoelasticity, the gasket 201 can be used as a bonding layer between the balloon body 1 and the hard linear segmentation part 3, which greatly improves the stability of fixing the linear segmentation part 3 on the surface of balloon body 1. The plastic with viscoelasticity may be but is not limited to a polyurethane elastomer, rubber, silica gel, silicone rubber, polyether block polyamide, styrene-isoprene-styrol copolymer or polyolefin elastomer.

Further, the gasket 201, the elastic tendons 202 and the sleeve rings 203 may be but are not limited to an integrally-formed structure.

Further, as illustrated in FIGS. 1 and 2, the gasket 201 has a long-strip shaped structure and extends along an axial direction of the balloon body 1, and a length of the gasket 201 is less than an axial length of the dilated straight working segment 101. The sleeve ring 203 is a circular ring structure, an inner diameter of the sleeve ring 203 matches an outer diameter of the thin-neck straight segment 103, so that the sleeve ring 203 can be sleeved outside of the thin-neck straight segment 103 and is fixed connected with the thin-neck straight segment 103, which can improve the stability of the gasket 201 on the surface of the balloon body 1 during dilation and swelling of the balloon body 1.

In the present disclosure, when assembling the elastic connector 2 and the balloon body 1, the sleeve ring 203 may be sleeved directly the outside of the thin-neck straight segment 103 at both ends of the balloon body 1, and then the sleeve ring 203 and the thin-neck straight segment 103 are connected into one piece through a hot fusion processing mode. When the balloon body 1 is in a dilation and swelling state, the dilated straight working segment 101 of the balloon body 1 will produce an outward first stress on the gasket 201, the stress being perpendicular to the balloon body 1, the elastic tendons 202 is stretched to become longer with dilation and swelling of the balloon body 1, the sleeve ring 203 with two fixed ends applies a tension on the corresponding gasket 201 through the two elastic tendons 202 respectively, the tension will produce an inward second stress on the gasket 201 perpendicular to the balloon body 1, a direction of the second stress is opposite to that of the first stress, thus the stability of fixing the gasket 201 on the surface of the dilated straight working segment 101 during dilation of the balloon body 1 can be greatly improved.

Exemplarily, a width of the gasket 201 is 0.3 mm to 5 mm, a thickness of the gasket 201 is 0.01 mm to 2 mm; and a width of the elastic tendons 202 is 0.15 mm to 2.5 mm.

In an optional embodiment of the present disclosure, as illustrated in FIG. 1 and FIG. 2, the linear segmentation part 3 has a long-strip shaped structure, a length of the linear segmentation part 3 is less than a length of the gasket 201, a width of the linear segmentation part 3 is less than a width of the gasket 201, the linear segmentation part 3 is fixed in a middle position of a surface of the gasket 201, and the linear segmentation part 3 extends along a length direction of the gasket 201. The linear segmentation part 3 may be formed through methods including but not limited to laser cutting, injection molding or 3D printing.

Further, a connection mode between the gasket 201 and the dilated straight working segment 101 of the balloon body 1 and the connection mode between the linear segmentation part 3 and the gasket may be but is not limited to thermal fusion, glue bonding or 3D printing.

Figure 3:
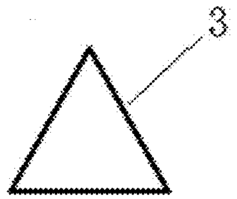
FIG. 3: a first cross section diagram of a linear segmentation part in a balloon catheter for linear segmentation of gland tissue in the present disclosure.
Figure 4:
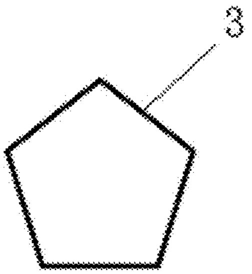
FIG. 4: a second cross section diagram of a linear segmentation part in a balloon catheter for linear segmentation of gland tissue in the present disclosure.
Figure 5:
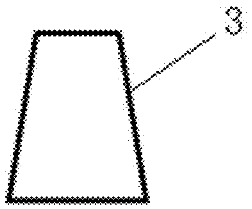
FIG. 5: a third cross section diagram of a linear segmentation part in a balloon catheter for linear segmentation of gland tissue in the present disclosure.

Further, as shown in FIGS. 3-5, a cross section of the linear segmentation part 3 is a polygon (such as a triangle, a diamond or a trapezoid), a distance from the top to the bottom of the cross section of the linear segmentation part 3 is 0.5 mm to 5 mm, and a width of a bottom of the cross section of the linear segmentation part 3 is less than 5 mm.

Further, the linear segmentation part 3 is made of a rigid-grade high molecular material or a metal material. Exemplarily, the high molecular material is PEEK (polyether-ether-ketone), HDPE (high density polyethylene), nylon, modified nylon or Pebax (a thermoplastic elastomer without containing a plasticizer); the metal material is medical stainless steel, cobalt-base alloy, nickel-titanium alloy or titanium alloy.

In an optional embodiment of the present disclosure, a surface of the balloon body 1 and/or a surface of the linear segmentation part 3 is/are coated with a drug layer, so as to provide a targeted drug to a glandular tissue for treatment.

The above contents are only schematic embodiments of the present disclosure and are not intended to limit the scope of the present disclosure. An equivalent change and amendment made by any person skilled in the art without deviating from the idea and principle of the present disclosure should fall into the scope protected by the present disclosure.

What is claimed is:

1. A balloon catheter for linear segmentation of gland tissue, wherein the balloon catheter for linear segmentation of gland tissue comprises a balloon body, an elastic connector and a linear segmentation part, wherein:

a middle portion of the elastic connector is fixed on a surface of the balloon body, the linear segmentation part is provided in the middle portion of the elastic connector, two ends of the elastic connector are fixedly connected with two ends of the balloon body respectively, and a position between the middle portion of the elastic connector and an end portion of the elastic connector is separated from the balloon body, wherein the balloon body comprises a dilated straight working segment, two transition segments and two thin-neck straight segments, the two transition segments are respectively located on two sides of the dilated straight working segment, one end of each of the two transition segments is connected with two ends of the dilated straight working segment respectively, and the other end of each of the two transition segments is connected with a corresponding one of the two thin-neck straight segments respectively;

a diameter of the dilated straight working segment is greater than a diameter of the thin-neck straight segments, and a diameter of the transition segments gradually decreases in a direction from the dilated straight working segment to the thin-neck straight segments; and wherein the elastic connector comprises a gasket, two elastic tendons and two sleeve rings, wherein the elastic connector is made of plastic with viscoelasticity, the gasket is fixed on a surface of the dilated straight working segment, the two sleeve rings are fixedly sleeved on the corresponding thin-neck straight segments respectively, one of the elastic tendons is connected between an end of the gasket and one of the sleeve rings, and the other one of the elastic tendons is connected between the other end of the gasket and the other one of the sleeve rings, the two elastic tendons are separated from the corresponding transition segments so that the elastic connector is in an active state, and the linear segmentation part is linear, and a radially innermost surface of the linear segmentation part contacts the gasket along an entire length of the linear segmentation part.

2. The balloon catheter for linear segmentation of gland tissue according to claim 1, wherein a length of the elastic connector in an axial direction of the balloon body is less than an axial length of the balloon body under a contraction state of the balloon body.

3. The balloon catheter for linear segmentation of gland tissue according to claim 1, wherein the gasket has a long-strip shaped structure and extends along an axial direction of the balloon body, and a length of the gasket is less than an axial length of the dilated straight working segment.

4. The balloon catheter for linear segmentation of gland tissue according to claim 3, wherein the linear segmentation part has a long-strip shaped structure, a length of the linear segmentation part is less than a length of the gasket, the linear segmentation part is fixed in a middle position of a surface of the gasket, and the linear segmentation part extends along a length direction of the gasket.

5. The balloon catheter for linear segmentation of gland tissue according to claim 3, wherein a cross section of the linear segmentation part is a polygon.

6. The balloon catheter for linear segmentation of gland tissue according to claim 5, wherein a distance from the top to the bottom of the cross section of the linear segmentation part is 0.5 mm to 5 mm, and a width of a bottom of the cross section of the linear segmentation part is less than 5 mm.

7. The balloon catheter for linear segmentation of gland tissue according to claim 1, wherein a surface of the balloon body and/or a surface of the linear segmentation part is/are coated with a drug layer.

* * * * *